United States Patent [19]

Hefner, Jr.

[11] Patent Number: 4,517,131

[45] Date of Patent: May 14, 1985

[54] HIGH YIELD PROCESS FOR THE CYANOALKYLATION OR AMIDOALKYLATION OR HYDROXYAROMATIC COMPOUNDS

[75] Inventor: Robert E. Hefner, Jr., Lake Jackson, Tex.

[73] Assignee: The Dow Chemical Company, Midland, Mich.

[21] Appl. No.: 301,170

[22] Filed: Sep. 11, 1981

[51] Int. Cl.$^3$ ............................................. C07C 121/75
[52] U.S. Cl. ................................ 260/465 F; 564/154; 564/156
[58] Field of Search .................... 260/465 F; 564/154, 564/156

[56] References Cited

U.S. PATENT DOCUMENTS 2,541,003  2/1951  Day et al. .................. 260/465 F X

OTHER PUBLICATIONS

Starks et al., Phase Transfer Catalysis–Principles and Techniques, pp. 133–138, (1978).

Primary Examiner—Dolph H. Torrence
Attorney, Agent, or Firm—Paul D. Hayhurst

[57] ABSTRACT

Hydroxyaromatic compounds are amido-alkylated or cyano-alkylated to form the corresponding compounds by:
  (a) heating said compounds with an alkylating agent in the presence of water and a catalyst, e.g., benzyltrimethylammonium chloride;
  (b) adding an alkaline agent, e.g., NaOH, to the heated mixture of (a); and
  (c) continuing to heat the resulting mixture until the corresponding amido- or cyano-alkylated compound is formed.

11 Claims, No Drawings

HIGH YIELD PROCESS FOR THE CYANOALKYLATION OR AMIDOALKYLATION OR HYDROXYAROMATIC COMPOUNDS

BACKGROUND OF THE INVENTION

This invention relates to the catalytic cyano-alkylation or amidoalkylation of hydroxyaromatic reactants and to compounds made thereby.

Compounds containing terminal amide or nitrile moieties are useful as precursors to carboxylic acids. Several routes to amido-alkylated hydroxyaromatic compounds are known. For example, a three-step method of synthesizing a di(amido-methylated)hydroquinone derivative is disclosed in *Chemical Abstracts*, Vol. 64, 17566e (1966). This three-step method involves reacting hydroquinone with chloroacetic acid, reacting the resulting carboxylic acid with thionyl chloride, and then reacting the next resulting acid chloride with ammonia to get p-phenylenedioxy diacetamide. It is also known to convert hydroquinone to a diester, which is then subjected to aminolysis to yield p-phenylenedioxy diacetamide. *Diss. Pharm. Pharmacol.*, Vol. 20, No. 6, 589–597 (1968).

U.S. Pat. No. 3,716,583 discloses, among other things, a non-catalytic method of forming amido-alkylated bisphenolic derivatives. The first step requires reacting a bisphenolic compound with an alkaline agent to form an alkaline salt. Then, an α-halogenated aliphatic acid derivative is added to start a condensation reaction, thereby forming an arylenedioxy dialkyleneamide.

Arylenedioxy dialkylenenitriles have also been prepared in the past. U.S. Pat. No. 4,061,777 discloses the non-catalytic reaction of α-chloroacetonitrile with substituted phenols to get the corresponding phenoxyacetonitrile. Similarly, alcohols were reacted with α-chloroacetonitrile in the presence of KOH and benzene to give alkoxynitriles. *Chemical Abstracts*, Vol. 85, 159369d (1976). Arylenedioxy dialkylenenitriles are also available via Michael addition of acrylonitrile to hydroxyaromatic compounds, however, yields are modest.

Heretofore, a high yield process for the catalytic monophasic amidoalkylation or cyanoalkylation of hydroxyaromatic compounds has not been disclosed.

SUMMARY OF THE INVENTION

In one aspect, the present invention is a process for alkylating hydroxyaromatic compounds by contacting a hydroxyaromatic reactant with an alkylating agent, as hereinafter defined, in the presence of a catalyst and a solvent, and subsequently adding an alkaline agent to the mixture under conditions sufficient to form the corresponding aromatic amide or nitrile. Surprisingly, the practice of said process requires only one step to convert a hydroxyaromatic reactant to the corresponding amide or nitrile in an aqueous, monophasic system. More importantly, the practice of said process produces products in yields much superior to the yields obtainable by the methods of the prior art, and obviates the need to employ a non-aqueous solvent. With few exceptions, the products produced are solids and are easily filtered from the reaction medium.

In another aspect, this invention is the discovery of novel compounds which may be prepared by the method of the present invention.

The products from the cyanoalkylation or amidoalkylation reactions of this invention are useful as chemical intermediates. Exemplary of this utility is the reaction of the amide products in a number of well-known reactions, such as the Hoffman degradation of amides and the hydrolysis of amides with acid or alkaline catalysis to form the corresponding carboxylic acids. The cyano-alkylated products of this invention are easily converted to amines by known methods and may be hydrolyzed by known methods to form carboxylic acids.

DETAILED DESCRIPTION OF THE INVENTION

Hydroxyaromatic compounds are suitably employed in the practice of this invention and are aromatic or alkylaromatic compounds which bear one or more hydroxy moieties. These compounds are generally represented by the formula $Ar\text{-}(OH)_n$ wherein n is at least one and Ar is a mono- or polyvalent organic radical. For non-polymeric hydroxyaromatic compounds, Ar is selected from the group consisting of: (a) aryl moieties having from 1 to 3, preferably from 1 to 2, aromatic rings; including fused ring systems, and (b) moieties of the formula

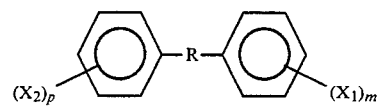

wherein R is optional and is selected from the group consisting of S, sulfoxide, sulfone, methylene, alkylidene, for example $C_1$ to $C_3$ alkylidene, O, and arylene; and wherein m and p have values independently from zero to 2; and wherein $X_1$ and $X_2$ are indpendently selected from the group consisting of Cl, Br, F, alkyl, nitro, and nitrile. Examples of these compounds include polyhydroxybenzenes, polyhydroxynaphthalenes, phenol, and bisphenol A and its alkylated derivatives. Preferred non-polymeric hydroxyaromatic reactants are aromatic compounds bearing at least two hydroxy moieties. Examples include dihydroxybenzenes, thiodiphenols, dihydroxybiphenyls, and halogenated derivatives of bisphenol A. The most preferred non-polymeric hydroxyaromatic reactants bear exactly two hydroxy moieties, e.g., p-dihydroxybenzene, m-dihydroxybenzene, 4,4'-thiodiphenol, 4,4'-dihydroxydiphenyl oxide and 3,3',5,5'-tetrabromo bisphenol A. Non-ortho isomers are preferred when the hydroxyaromatic reactant has only one aromatic ring. The hydroxyaromatic reactants may bear groups or substituents which do not interfere with the amidoalkylation or cyanoalkylation reaction. Examples of these substituents include nitro, nitrile, alkoxy, alkyl, alkenyl, Cl, Br, F and the like. An example of such a hydroxyaromatic reactant is p-chlorophenol.

Hydroxyaromatic compounds may also be polymers, including oligomers, which bear one or more hydroxy moieties. Examples of polymeric hydroxyaromatic reactants include phenol formaldehyde polymers, with the novolaks being preferred, and resorcinol formaldehyde polymers. Preferred polymeric hydroxyaromatic reactants are represented by the formula:

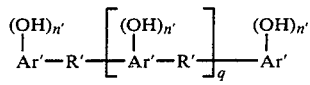

wherein R' is $C_1$–$C_3$ alkylene; n' is individually selected from 0, 1 or 2; Ar' is a mono- or polyvalent organic radical selected from moieties having from 1 to 2 aromatic rings; and q is at least one.

The most preferred polymeric hydroxyaromatic reactants are represented by the foregoing formula wherein q is from 1 to about 12, R' is methylene, n' is 1, and Ar' is a hydrocarbon aromatic single ring.

Mixtures of polymeric hydroxyaromatic reactants are also operable. For example, a polymer mixture wherein the average molecular weight is 395 g/mole and wherein q varies is a most preferred hydroxyaromatic reactant.

The alkylating agents employed in the practice of this invention are haloamidohydrocarbylenes or halocyanohydrocarbylenes. The preferred alkylating agents are generally represented by formula I:

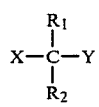   I wherein X is a halogen; $R_1$ and $R_2$ are independently H or $C_1$–$C_{10}$ alkyl; Y is —C≡N or

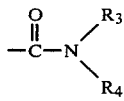

wherein $R_3$ and $R_4$ are independently H or $C_1$–$C_{10}$ alkyl. Preferably, X is Cl or Br, and $R_1$, $R_2$, $R_3$ and $R_4$ are H or $C_1$–$C_3$ alkyl. Examples of preferred alkylating agents include 2-chloropropionamide and 2-chloropropionitrile. The most preferred alkylating agents are 2-chloroacetamide and α-chloroacetonitrile.

The amount of alkylating agent employed is partially dependent on the number of hydroxy moieties on the hydroxyaromatic reactant. The alkylating agent is usually employed in an amount which will provide an alkylating agent/hydroxy moiety molar ratio of from about 1.5 to about 4. Preferably this ratio will be from about 2.5 to about 3.

An alkaline agent is employed in the practice of the present invention for the purpose of increasing conversion to the cyano- or amido- alkylated product. The alkaline agent may be an alkali metal hydroxide or an alkaline earth metal hydroxide. Preferred alkaline agents are KOH, NaOH or mixtures thereof. Sodium hydroxide is the most preferred alkaline agent. The alkaline agent is typically employed in order to provide a ratio of from about 1 to about 2 moles of alkali metal hydroxide per mole of hydroxy moieties originally present on the hydroxyaromatic reactant. Preferably this ratio will be from about 1.1 to about 1.5.

Water is typically employed in the process of this invention for the purpose of providing a suitable reaction medium. This allows the reaction to be carried out in one phase and subsequently allows the removal of the reaction product as a filterable solid, except for rare cases in which the product is a liquid as is the case when the hydroxyaromatic reactant is bisphenol A.

The catalyst may be a quaternary ammonium salt. Quaternary ammonium halides are preferred catalysts. Benzyltrialkyl ammonium halides, such as benzyltrimethyl ammonium halides, are the most preferred catalysts. The catalyst may be a quaternary phosphonium salt when Y is —C≡N. Typically, from about 0.001 to about 0.25 moles of catalyst are employed per mole of hydroxy moiety of the hydroxyaromatic reactant. Preferably, from about 0.01 to about 0.10 moles of catalyst are employed per mole of hydroxy moiety of the hydroxyaromatic reactant.

Catalytic quaternary salts may be bound in a polymeric support in the form of ion-exchange resins. Typical ion-exchange resins are those which bear quaternary ammonium salts on macroporous styrene-divinylbenzene resins. Examples of these bound quaternary salts include Dowex® MSA-1 and the like. The ion-exchange resin form of catalyst is advantageous in that it is easily recovered or, if used in a fixed bed, obviates the need for a catalyst recovery step. It should be noted that a catalyst bound in a polymeric support generally will not go into solution. Thus, for the purposes of this invention, a monophasic solution may contain solid particles of bound catalyst. Preferably, when solid particles of bound catalyst are employed, they will be uniformly dispersed in the reaction mixture or will form a fixed bed.

The reactants may be added in any order desired, except for the alkaline agent. Preferably, the alkaline agent is added as an aqueous solution. The alkaline agent preferably is added only after the reaction mixture containing the hydroxyaromatic reactant, the alkylating agent, the catalyst and the water or a portion thereof, has been heated to the desired prereaction temperature and the aforementioned ingredients have formed a monophasic solution. The alkaline agent may be added before a monophasic solution forms, i.e., while the aforementioned ingredients are in the form of a slurry. At some point during the addition of the alkaline agent to a non-monophasic mixture, a monophasic solution will be formed. Preferably, the reaction mixture is further heated for the desired time after the alkaline agent has been added.

The reaction is preferably conducted at reflux temperatures, although higher or lower temperatures may be employed if desired. The reaction time depends on the temperature employed and usually takes between about 1 and about 24 hours; preferably it takes between about 4 and about 8 hours.

When the reactants, catalyst and water are properly combined under reaction conditions as hereinbefore specified, a product mixture will be formed. In most cases this mixture will contain the product in (micro)-crystalline form. The solid product may be separated by direct filtration from the non-product portions of the reaction mixture. Washing of the solid product is often beneficial. In some cases the product will be in liquid form. Liquid products, such as di(cyano-methylated)-bisphenol A, may be recovered by conventional means such as decantation or solvent extraction.

At least one component of the product mixture will be amido- or cyano-alkylated and will correspond structurally to the particular hydroxyaromatic reactant used as a starting material. The products formed are generally represented by the formula

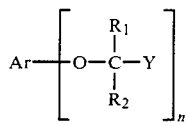

wherein n is at least one; Ar, $R_1$, $R_2$ and Y are as previously defined.

For the purposes of this invention, alkyl, arylene, methylene and alkylidene moieties may be substituted with other moieties which do not interfere with the cyanoalkylation or amidoalkylation reaction.

The following examples are given to illustrate the invention and should not be construed as limiting its scope. All percentages in the examples are by weight unless otherwise indicated.

I. VARIATION OF THE HYDROXYAROMATIC REACTANT

EXAMPLE 1

Six-tenths of a mole of 2-chloroacetamide, hydroquinone (0.10 mole), benzyltrimethylammonium chloride catalyst (0.04 mole), and water (25.0 g) are added with stirring to a reactor under a nitrogen atmosphere. The reactor is heated and the stirred slurry becomes a clear light brown solution between the temperatures of 70° C.–75° C. The temperature is allowed to stabilize at 110° C., the 0.40 mole of sodium hydroxide dissolved in 25.0 g of water is added to the stirred solution. A light tan colored slurry forms and the reaction is continued at 110° C. for a total of 1.1 hours. The reactor is allowed to cool to room temperature and the product is recovered as a wet filter cake. The wet crude product is slurried into 100 g of water and is heated to 100° C. It is held at this temperature for 15 minutes. Filtration of the hot slurry is followed by vacuum drying, providing an 83.9 percent isolated yield of di(amido-methylated)hydroquinone.

EXAMPLE 2

A reaction is completed using the method of Example 1 except that tetrabromobisphenol A (0.10 mole) is used in place of hydroquinone, the amount of water is increased to 50.0 g, and the reaction time is increased to 3.0 hours. Di(amido-methylated)tetrabromobisphenol A is isolated in 99.3 percent yield.

EXAMPLE 3

A reaction is done using the method of Example 1 except that 1,3-dihydroxybenzene (resorcinol) (0.10 mole) is used in place of hydroquinone and the reaction time is increased to 2.0 hours with a 112° C. reaction temperature. Di(amido-methylated)resorcinol is isolated in 83.4 percent yield.

EXAMPLE 4

A reaction is done using the method of Example 1 except that 4,4'-thiodiphenol (0.10 mole) is used in place of hydroquinone, the amount of water is increased to 35.0 g and the reaction time is increased to 1.2 hours with a 112° C. reaction temperature. Di(amido-methylated) 4,4'-thiodiphenol is isolated in 87.6 percent yield.

EXAMPLE 5

Two reactions are done using the method of Example 1 except that 1,2-dihydroxybenzene (catechol) (0.10 mole) is used in place of hydroquinone and the reaction time of the first reaction is 3 hours while the reaction time of the second reaction is 16 hours with a 114° C. reaction temperature. After cooling the reactor to room temperature (21° C.), the slurry is held at this temperature for 3 hours without further stirring. The filtered product is washed with the minimum of water required to reestablish a slurry. The slurry is then vacuum dried at 85° C. for 24 hours to a constant weight, and is then analyzed using nuclear magnetic resonance spectroscopy. The product (18.2 g) of the first reaction contains 65.4 percent monoamide and 34.6 percent diamide. The second reaction provides a 98.4 percent isolated yield of di(amido-methylated) 1,2-dihydroxybenzene.

EXAMPLE 6

One-tenth of a mole of 4,4'-dihydroxybiphenyl, α-chloroacetonitrile (0.60 mole) and 60 percent aqueous benzyltrimethylammonium chloride catalyst (0.04 mole) are added to a reactor under a nitrogen atmosphere. The reactor is heated to 92° C. then sodium hydroxide (0.40 mole) dissolved in water (60.0 g) is added to the fine stirred slurry over a 23-minute period. The initial aqueous sodium hydroxide addition induces formation of a clear brown refluxing solution. The reaction continues at 90° C. to 95° C. for a total of 80 minutes. The reactor is allowed to cool and once 70° C. to 75° C. is reached, a crystalline slurry forms. After chilling to 4° C. for 1 hour, filtration followed by multiple hot water washing of the filter cake and vacuum drying provides the di(cyano-methylated) product in 99.6 percent yield. The product was analyzed by gas chromatography and nuclear magnetic resonance spectroscopy. A sample of the di(cyano-methylated) product is recrystallized from 1,4-dioxane providing transparent needles.

EXAMPLE 7

A reaction is completed using the method of Example 6, except that 4,4'-thiodiphenol (0.10 mole) is used as the hydroxyaromatic reactant. The reaction temperature is allowed to stabilize at 82° C. and the aqueous sodium hydroxide is added to the clear solution over a 26-minute period. A stirred crystalline slurry forms after 36 minutes of reaction. The reaction continues at 89° C. to 94° C. for a total of 99 minutes. The di(cyano-methylated) product is obtained in 96.2 percent yield as crystalline plates. A sample of the di(cyano-methylated) product is recrystallized from methanol providing transparent plates.

EXAMPLE 8

A reaction is completed using the method of Example 6, except that 4,4'-sulfonyldiphenol (0.10 mole) is used as the hydroxyaromatic reactant. The reaction temperature is allowed to stabilize at 87° C. and the aqueous sodium hydroxide is added to the clear solution over a 31-minute period. A crystalline slurry forms after 46 minutes of reaction at 88° C. to 99° C. and the cooling is started. The di(cyano-methylated) product is obtained in 96.8 percent yield.

EXAMPLE 9

A reaction is performed using the method of Example 6, except that 1,4-dihydroxybenzene (hydroquinone) (0.10 mole) is used as the hydroxyaromatic reactant. The reaction temperature is allowed to stabilize at 78°

C. and the aqueous sodium hydroxide is added to the clear solution over a 27-minute period. The reaction continues at 93° C. to 99° C. for a total of 188 minutes. The reactor is allowed to cool and once 50° C.–55° C. is reached, a crystalline slurry forms. A washing step employing 20 percent aqueous sodium hydroxide is employed in addition to the usual hot water washing. A 77.6 percent yield of di(cyano-methylated) product is obtained.

EXAMPLE 10

A reaction is performed using the method of Example 6, except that 2,7-naphthalenediol (0.10 mole) is used as the hydroxyaromatic reactant. The reaction temperature is allowed to stabilize at 75° C. and the aqueous sodium hydroxide is added to the clear solution over a 31-minute period. The reaction continues at 88° C. to 95° C. for a total of 173 minutes. The reactor is chilled for 3 hours at 4° C. A washing step employing 20 percent aqueous sodium hydroxide is employed in addition to the usual hot water washing. A 89.2 percent yield of di(cyano-methylated) product is obtained.

EXAMPLE 11

A reaction is performed using the method of Example 6, except that 3,3',5,5'-tetrabromo-4,4'-isopropylidenediphenol is used as the hydroxyaromatic reactant and 0.80 mole of α-chloroacetonitrile is used. The reaction temperature is allowed to stabilize at 85° C. and the aqueous sodium hydroxide is added to the clear solution over a 117-minute period. The reaction continues at 85° C. to 95° C. for a total of 290 minutes. The reactor is allowed to cool to room temperature (21° C.), the reaction crude is devolatilized to remove unreacted α-chloroacetonitrile and some of the water, and the off-white di(cyano-methylated) product is recovered after multiple hot water washing in 99.7 percent yield.

EXAMPLE 12

Forty-one thousandths of a mole of 3,3',5,5'-tetrachloro-4,4'-dihydroxybiphenyl, α-chloroacetonitrile (0.40 mole) and 60 percent aqueous benzyltrimethylammonium chloride catalyst (0.0164 mole) are added to a reactor under a nitrogen atmosphere. The reactor is heated to 86° C. then sodium hydroxide (0.123 mole) dissolved in water (18.5 g) is added to the fine stirred slurry over a 9-minute period. The initial aqueous sodium hydroxide addition induces formation of a clear brown refluxing solution. A crystalline slurry forms after 25 minutes of reaction at 95° C. to 97° C. and the cooling is started 3 minutes later. After chilling to 4° C. for 30 minutes, filtration followed by washing with 10 percent aqueous sodium hydroxide and hot water then vacuum drying provides the di(cyano-methylated) product in 99.1 percent yield.

EXAMPLE 13

1,2-Dihydroxybenzene (pyrocatechol) (0.0824 mole), α-chloroacetonitrile (0.4944 mole) and 60 percent aqueous benzyltrimethylammonium chloride catalyst (0.033 mole) are added with stirring to a reactor under a nitrogen atmosphere. The reactor is heated to 94° C. then sodium hydroxide (0.247 mole), dissolved in water (37.1 g) is added to the clear solution over a 10-minute period. The reaction continues at 93° C. to 94° C. for a total of 113 minutes. After chilling to 4° C. for 1 hour, 10 percent aqueous sodium hydroxide and hot water washing then vacuum drying provides the di(cyano-methylated) product in 70.1 percent yield.

EXAMPLE 14

A reaction is completed using the method of Example 13, except that 1,3-dihydroxybenzene (resorcinol) (0.0824 mole) is used as the hydroxyaromatic reactant. The reaction temperature is allowed to stabilize at 94° C. and the aqueous sodium hydroxide is added to the clear solution over a 24-minute period. The reaction continues at 93° C. to 95° C. for a total of 111 minutes. The di(cyano-methylated) product is obtained in 94.8 percent yield as crystalline plates. Of the three isomeric dihydroxybenzene reactants employed (see also Examples 9 and 13), the highest yield of di(cyano-methylated) product is obtained in this example using the 1,3-dihydroxy isomer.

EXAMPLE 15

2,2',4,4'-Tetrahydroxydiphenyl sulfide (0.0824 mole), α-chloroacetonitrile (0.9888 mole) and 60 percent aqueous benzyltrimethylammonium chloride catalyst (0.066 mole) are added to a reactor under a nitrogen atmosphere. The reactor is heated and the stirred slurry becomes a clear solution at room temperature (21° C.). The temperature is allowed to stabilize at 80° C., then 0.494 mole of sodium hydroxide dissolved in 74.2 g of water is added over a 20-minute period to the stirred solution. The reaction continues at 95° C. for a total of 92 minutes, after which time a crystalline slurry forms. After chilling to 4° C. for 1 hour, filtration followed by washing with 20 percent aqueous sodium hydroxide and hot water then vacuum drying provides the tetra(cyano-methylated) product in 99.9 percent yield.

EXAMPLE 16

A novolak oligomer (0.05 mole), α-chloroacetonitrile (0.60 mole) and 60 percent aqueous benzyltrimethylammonium chloride catalyst (0.04 mole) are added to a reactor under a nitrogen atmosphere. The novolak oligomer possesses the following structure where both ortho and para isomeric structures are present:

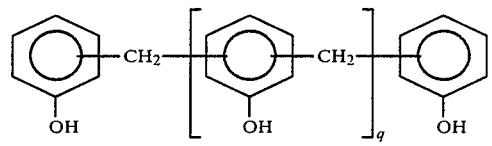

wherein q is an integer and may vary from molecule to molecule. Gel permeation chromatography demonstrates an average molecular weight of 395. The reactor is heated and the stirred mixture becomes a homogeneous solution at 35° C. The temperature is allowed to stabilize at 98° C., then 0.30 mole of sodium hydroxide dissolved in 45.0 g of water is added over a 12-minute period to the stirred solution. The reaction continues at 95° C. for a total of 145 minutes. The reactor is allowed to cool to room temperature (21° C.) and the product is recovered by extraction into hot chloroform. The combined chloroform extracts are devolatilized to remove chloroform and the recovered poly(cyano-methylated) oil product is weighed and analyzed by nuclear magnetic resonance spectroscopy. A 92.3 percent isolated yield of polycyano-methylated product is obtained.

Exhaustive cyanomethylation is indicated by the lack of hydroxyl protons in the NMR analysis.

EXAMPLE 17

One-tenth of a mole of 4,4'-isopropylidenediphenol (sold by the The Dow Chemical Company under the name Parabis ® resin intermediate), α-chloroacetonitrile (0.60 mole) and 60 percent aqueous benzyltrimethylammonium chloride catalyst (0.04 mole) are added to a reactor under a nitrogen atmosphere. The reactor is heated and the stirred slurry becomes a clear solution at 32° C. The temperature is allowed to stabilize at 52° C. then 0.40 mole of sodium hydroxide dissolved in 60.0 g of water is added over a 186-minute period to the stirred solution. The reaction continues at 49° C. to 52° C. for a total of 65 hours. The reactor is allowed to cool to room temperature (22° C.) and the product is recovered by extraction into chloroform. The combined chloroform extracts are devolatilized to remove chloroform and the remaining oil is washed with 20 percent aqueous sodium hydroxide followed by washing with water. The resulting oil is again extracted into chloroform, dried with anhydrous sodium sulfate, filtered, devolatilized to remove chloroform, weighed, and analyzed by nuclear magnetic resonance spectroscopy and gas chromatography. A 98.6 percent isolated yield of high purity di(cyano-methylated) product is obtained.

EXAMPLE 18

(Not an embodiment of this invention)

A reaction is completed using the method of Example 6, except that 3,3',5,5'-tetra-t-butyl-4,4'-dihydroxybiphenyl was used as the hydroxyaromatic reactant and 0.80 mole of α-chloroacetonitrile and 0.02 mole of 60 percent aqueous benzyltrimethylammonium chloride catalyst are used. The reactor is heated to 101° C. then sodium hydroxide (0.30 mole) dissolved in water (95.0 g) is added to the clear stirred solution over a 6-minute period. A slurry forms after 19 minutes of reaction at 97° C. to 101° C. The reaction continues at 95° C. to 98° C. for a total of 55 minutes. Only the unreacted dihydroxyaromatic reactant is recovered. This lack of cyanomethylation is attributed to the steric hindrance of the hydroxyl groups induced by the pairs of ortho t-butyl radicals.

II. VARIATION OF THE CATALYST

EXAMPLE 19

One-fourth of a mole of 2-chloroacetamide, hydroquinone (0.10 mole), catalyst (0.02 mole) and water (12.8 g) are added with stirring to a reactor under a nitrogen atmosphere. The reactor is heated and the stirred slurry becomes a clear light brown solution between the temperatures of 70° C.–75° C. The temperature is allowed to stabilize at 107° C., then 0.40 mole of sodium hydroxide dissolved in 25.0 g of water is added over a 3-minute period to the stirred solution. After 87.5 percent of the sodium hydroxide solution is added, a light tan colored stirred slurry forms. The reaction continues at 107° C. for a total of 4 hours. The reactor is allowed to cool to room temperature (21° C.) and the slurry is held at this temperature for 3 hours without further stirring. The product is filtered and then is vacuum dried at 85° C. for 24 hours to a constant weight. The product is then analyzed using nuclear magnetic resonance spectroscopy (NMR). The results are reported in Table I.

TABLE I

| | Amidomethylation of Hydroquinone | | | |
|---|---|---|---|---|
| | Product Composition (%) | | | |
| Catalyst | Hydroquinone | Mono(amidomethylated) Hydroquinone | Di(amidomethylated) Hydroquinone | Recovered Product (g) |
| Benzyltrimethylammonium chloride | none | 3.36 | 96.64 | 22.3 |
| Tetrahydroxymethylphosphonium chloride | 9.00 | 25.00 | 66.00 | 18.2 |
| Tetramethylammonium chloride | 3.59 | 14.87 | 81.54 | 22.4 |
| None* | 9.40 | 15.67 | 74.92 | 20.8 |

*Comparative Example - Not an embodiment of this invention.

The best results are obtained with the benzyltrimethylammonium chloride catalyst; no unreacted hydroquinone is present in the product and the highest amount of di(amide-methylated) product is produced. Tetramethylammonium chloride catalyst provides the second highest amount of di(amide-methylated) product and the second lowest amount of residual unreacted hydroquinone. The phosphonium halide catalyst, tetrahydroxymethylphosphonium chloride gives an increased amount of mono(amido-methylated)hydroquinone, thereby unsatisfactorily lowering the di(amide-methylated) product yield below that of the non-catalytic run.

EXAMPLE 20

Two reactions are done using the method of Example 19, except that the reaction temperature is allowed to stabilize at 110° C., the 0.25 mole of sodium hydroxide dissolved in 13.0 g of water is added to the stirred solution over a 3-minute period. The total reaction time is shortened to 0.3 hour at 110° C. temperature. In one reaction the catalyst is benzyltrimethylammonium chloride. In the other reaction no catalyst is employed. The results are reported in Table II.

TABLE II

| | Product Composition (%) | | | |
|---|---|---|---|---|
| Catalyst | Hydroquinone | Mono(amidomethylated) Hydroquinone | Di(amidomethylated) Hydroquinone | Recovered Product (g) |
| Benzyltrimethylammonium chloride | 6.81 | 20.22 | 72.97 | 20.7 |
| None* | 12.32 | 38.12 | 49.56 | 18.3 |

*Comparative Example - Not an embodiment of this invention.

EXAMPLE 21

A pair of reactions are completed as follows
(A) One-tenth of a mole of p-chlorophenol, α-chloroacetonitrile (0.30 mole) and 60 percent aqueous benzyltrimethylammonium chloride catalyst (0.01 mole) are added to a reactor under a nitrogen atmosphere. The reactor is heated and the temperature is allowed to stabilize at 81° C. then 0.20 mole of sodium hydroxide dissolved in 30.0 g of water is added over a 17-minute period to the stirred clear solution. The reaction continues at 88° C. to 95° C. for a total of 104 minutes. After chilling to 4° C. for 4 hours, 10 percent aqueous sodium hydroxide and hot water washing then vacuum drying provides the cyanoalkylated product in quantitative yield.

(B) A comparative example (not an embodiment of this invention) is completed by adding p-chlorophenol (0.1 mole) and α-chloroacetonitrile to a reactor under a nitrogen atmosphere. The reactor is heated and the temperature is allowed to stabilize at 55° C. then 0.20 mole of sodium hydroxide dissolved in 30.0 g of water is added over a 38-minute period to the stirred clear solution. The reaction continues at 62° C. to 98° C. for a total of 17.3 hours. The product is analyzed by gas chromatography demonstrating less than 40 percent conversion of the hydroxyaromatic reactant to the cyanoalkylated product. Substantial unreacted α-chloroacetonitrile is also observed.

The non-catalytic reaction of comparative Example 21(B) stagnates with respect to conversion resulting in a low yield of the cyanoalkylated product when compared to the catalytic reaction of Example 21(A).

EXAMPLE 22

A pair of reactions are performed using the method of Example 6, except that 3,3',5,5'-tetrabromo-4,4'-isopropylidenediphenol is used as the hydroxyaromatic reactant. In the first reaction, 0.04 mole of tetramethylammonium chloride is used as the catalyst. The reaction temperature is allowed to stabilize at 75° C. and the aqueous sodium hydroxide is added to the clear solution over a 33-minute period. The reaction continues at 75° C. to 97° C. for a total of 146 minutes. In the second reaction, only 0.004 mole of tetramethylammonium chloride is used as the catalyst. The reaction temperature is allowed to stabilize at 82° C. and the aqueous sodium hydroxide is added to the stirred slurry over a 31-minute period. The reaction continues at 75° C. to 96° C. for a total of 107 minutes. The di(cyano-methylated) product is obtained in quantitative yield from the first reaction and 99.4 percent yield from the second reaction.

The efficacy of a range of catalyst loadings is illustrated in this example, in spite of the fact that differences in the appearance of the reactant mixture (solution versus slurry) occurs.

EXAMPLE 23

The reaction of Example 6 is repeated using Dowex ® MSA-1 ion-exchange resin in the chloride form (9.31 g) in place of the benzyltrimethylammonium chloride catalyst of Example 6. The reactor is heated to 87° C. then sodium hydroxide (0.30 mole) dissolved in water (45.0 g) is added to the fine slurry over a 20-minute period. The initial aqueous sodium hydroxide addition induces formation of a clear brown refluxing solution containing the suspended resin bead catalyst. The reaction continues at 94° C. to 96° C. for a total of 100 minutes. The reaction product is filtered hot to remove the resin bead catalyst followed by chilling of the filtrate at 4° C. for 1 hour. Washing of the filter cake with 20 percent aqueous sodium hydroxide and hot water is followed by vacuum drying to give the di(cyano-methylated) product in 99.2 percent yield.

EXAMPLE 24

A reaction is performed using the method of Example 6, except that 3,3',5,5'-tetrabromo-4,4'-isopropylidenediphenol is used as the hydroxyaromatic reactant and tetra-n-butylphosphonium bromide catalyst (0.01 mole) is used in place of the benzyltrimethylammonium chloride catalyst of Example 6. The reactor is heated to 92° C. and then sodium hydroxide (0.30 mole) dissolved in water (45.0 g) is added to the stirred clear solution over an 11-minute period. The reaction continues at 95° C. to 98° C. for a total of 88 minutes. After chilling to 4° C. for 1 hour, filtration followed by washing with 20 percent aqueous sodium hydroxide and hot water then vacuum drying provides the di(cyano-methylated) product in 99.7 percent yield. The efficacy of tetrasubstituted phosphonium salt catalysts in the cyanoalkylation reactions of this invention is supported via this example.

EXAMPLE 25

The reaction of Example 17 is repeated using Dowex ® MSA-1 ion-exchange resin in the chloride form (9.31 g) in place of the benzyltrimethylammonium chloride catalyst of Example 17. The reactor is heated to 85° C. then sodium hydroxide (0.40 mole) dissolved in water (45.0 g) is added to the clear stirred solution containing suspended resin bead catalyst. The reaction continues at 95° C. to 100° C. for a total of 127 minutes. The reactor is allowed to cool to room temperature (21° C.), diluted with 100.0 g of water, and extracted with hot chloroform. The combined chloroform extracts are filtered to remove suspended resin bead catalyst then washed with 10 percent aqueous sodium hydroxide and devolatilized to remove chloroform, weighed, and analyzed by gas chromatography. A 84.1 percent isolated yield of high purity di(cyano-methylated) product is obtained as an oil.

III. VARIATION OF ALKYLATING AGENT

EXAMPLE 26

A reaction is done using the method of Example 19, except that 2-chloropropionamide (0.25 mole) is substituted for 2-chloroacetamide. The catalyst is benzyltrimethylammonium chloride. The di(amido-alkylated) product is recovered in 92.4 percent isolated yield.

EXAMPLE 27

One-tenth of a mole of 3,3',5,5'-tetrabromo-4,4'-isopropylidenediphenol, 2-chloropropionitrile (0.553 mole) and 60 percent aqueous benzyltrimethylammonium chloride catalyst (0.04 mole) are added to a reactor under a nitrogen atmosphere. The reactor is heated to 80° C. then sodium hydroxide (0.30 mole) dissolved in water (45.0 g) is added to the stirred clear solution over a 35-minute period. The reaction continues at 92° C. to 94° C. for a total of 17 hours. The reactor is allowed to cool and once 80° C. to 85° C. is reached, a viscous oil layer separates. After chilling to 4° C. for 1 hour, the water is decanted off and 10 percent aqueous sodium hydroxide (200 g) is used to wash the oil followed by washing with hot water. A crystalline solid forms after water washing and is recovered by filtration and vacuum dried to provide the di(cyanoalkylated) product in quantitative yield.

EXAMPLE 28

(Not an embodiment of this invention)

A reaction is done using the method of Example 19, except that 3-chloropropionamide (0.25 mole) is substituted for 2-chloroacetamide and the reaction time is increased to 16.3 hours. The catalyst is benzyltrimethylammonium chloride. No mono- or di(amidomethylated) product was produced.

EXAMPLE 29

(Not an embodiment of this invention)

A pair of reactions are completed using 3,3',5,5'-tetrabromo-4,4'-isopropylidenediphenol (0.10 mole) and 3-chloropropionitrile (0.60 mole). In the first reaction, 60 percent aqueous benzyltrimethylammonium chloride (0.04 mole) is used as the catalyst. The reaction temperature is allowed to stabilize at 113° C. and aqueous sodium hydroxide (0.30 mole) dissolved in 45.0 g of water is added to the clear solution over a 71-minute period. The reaction continues at 90° C. to 92° C. for a total of 17 hours. In the second reaction, tetramethylammonium chloride catalyst (0.02 mole) is used. The reaction temperature is allowed to stabilize at 94° C. and the aqueous sodium hydroxide is added to the clear solution over a 22-minute period. The reaction continues at 92° C. to 93° C. for a total of 93 minutes. The reaction products are recovered using the method described in Example 6 and analyzed by nuclear magnetic resonance spectroscopy. Only unreacted 3,3',5,5'-tetrabromo-4,4'-isopropylidenediphenol is recovered from each of these reactions. Considering these results, only α-halogenonitrile reactants are suitable for use in the cyanoalkylation reaction of this invention.

EXAMPLE 30

(Not an embodiment of this invention)

A reaction is completed using the method of Example 29, except that 3-bromopropionitrile (0.60 mole) is substituted for 3-chloropropionitrile. 60 Percent aqueous benzyltrimethylammonium chloride (0.04 mole) is used as the catalyst. The reaction temperature is allowed to stabilize at 91° C. and aqueous sodium hydroxide is added to the clear solution over a 10-minute period. The reaction continues at 94° C. for a total of 21 hours. Only unreacted 3,3',5,5'-tetrabromo-4,4'-isopropylidenediphenol is recovered from this reaction.

IV. MISCELLANEOUS

EXAMPLE 31

A pair of reactions are done using the method of Example 19 with the following stoichiometry:

| | |
|---|---|
| 2-chloroacetamide | 2.00 moles |
| hydroquinone | 0.50 mole |
| benzyltrimethylammonium chloride | 0.10 mole |
| water | 83.5 g |

In both reactions, the temperature is allowed to stabilize at 110° C., then 2.00 moles of sodium hydroxide dissolved in 125.0 g of water is added to the stirred solution. In the first reaction, the aqueous sodium hydroxide is added over a 98-minute period followed by 142 minutes of reaction. In the second reaction, the aqueous sodium hydroxide is added over a 3-minute period followed by 237 minutes of reaction. The results are reported in Table III.

TABLE III

| Sodium Hydroxide Addition Time (min) | Reaction Time (min) | Total Reaction Time (min) | Product Composition (%) | | | Recovered Product (g) |
|---|---|---|---|---|---|---|
| | | | Hydroquinone | Mono-(amidomethylated) Hydroquinone | Di-(amidomethylated) Hydroquinone | |
| 98 | 142 | 240 | 24.24 | 50.51 | 25.25 | 83.4 |
| 3 | 237 | 240 | none | 3.14 | 96.86 | 109.5 |

Much better diamidoalkylation results are obtained when the NaOH is rapidly added; reaction time is greatly reduced.

EXAMPLE 32

(Not an embodiment of this invention)

The reaction of Example 17 is repeated using Dowex ® MSA-1 ion-exchange resin in the chloride form (9.31 g) and Dowex ® MSA-1 ion-exchange resin in the hydroxide form (45.0 g). No alkaline agent is used in this reaction. The reactor is heated and the clear stirred solution containing suspended resin bead catalyst is held at 93° C. for a total of 6.4 hours. A series of samples are taken after 1.4, 3.4 and 6.4 hours of reaction and analyzed by gas chromatography. In every case only about 15 percent of the 4,4'-isopropylidenediphenol is converted to product containing in excess of 95 percent mono(cyano-methylated) starting material. Substantial unreacted α-chloroacetonitrile is also observed.

EXAMPLE 33

(Not an embodiment of this invention)

A series of comparative examples illustrative of various prior art methods are completed as follows (A) One-tenth of a mole of 4,4'-isopropylidenediphenol and 1,4-dioxane (70.0 ml) are added to a reactor. The reactor is heated and solid potassium carbonate (0.20 mole) and water (40.0 g) are added. Heating is continued and a clear solution forms at 60° C. The temperature is allowed to stabilize at 75° C., then α-chloroacetonitrile (0.20 mole) is added over a 5-minute period to the stirred solution. The reaction continues at 75° C. for a total of 16 hours. The reactor is allowed to cool to room temperature (22° C.) and the product is devolatilized to remove 1,4-dioxane and some water. Extraction with methyl ethyl ketone provides a solution of oil product which is analyzed by gas chromatography, demonstrating about 25 percent conversion of 4,4'-isopropylidenediphenol to an 80 percent mono(cyano-methylated) and 20 percent di(cyano-methylated) product. Substantial unreacted α-chloroacetonitrile is also observed.

(B) One-tenth of a mole of 4,4'-isopropylidenediphenol and methyl ethyl ketone (50.0 ml) are added to a reactor. A solution of potassium carbonate (0.20 mole) and water (40.0 g) is added and the reactor is heated. Heating is continued and the temperature of the stirred clear solution is allowed to stabilize at 74° C., then α-chloroacetonitrile (0.50 mole) is added over a 4-minute period. The reaction continues at a final temperature of 80° C. for a total of 46 hours. A series of samples are taken after 18, 23, and 46 hours of reaction and analyzed by gas chromatography to provide the following results:

| Sample Time (hr) | 4,4'-isopropyl-idenediphenol (%) | mono(cyano-methylated) (%) | di(cyano-methylated) (%) |
| --- | --- | --- | --- |
| 18 | 45 | 45 | 10 |
| 23 | 46 | 43 | 11 |
| 46 | 38 | 48 | 14 |

Substantial unreacted α-chloroacetonitrile is also observed.

(C) One-tenth of a mole of 4,4'-isopropylidenediphenol and methyl ethyl ketone (50.0 ml) are added to a reactor. The reactor is heated and a solution of sodium hydroxide (0.20 mole) and water (80.0 g) is added. Heating is continued and the temperature of the stirred clear solution is allowed to stabilize at 76° C., then α-chloroacetonitrile (0.30 mole) is added over a 14-minute period. The reaction continues at a final temperature of 80° C. for a total of 25.5 hours. A series of samples are taken after 16.5, 21.5 and 25.5 hours of reaction and analyzed by gas chromatography to provide the following results:

| Sample Time (hr) | 4,4'-isopropyl-idenediphenol (%) | mono(cyano-methylated) (%) | di(cyano-methylated) (%) |
| --- | --- | --- | --- |
| 16.5 | 50 | 44 | 6 |
| 21.5 | 50 | 44 | 6 |
| 25.5 | 51 | 44 | 5 |

Substantial unreacted α-chloroacetonitrile is also observed.

(D) One-tenth of a mole of 4,4'-isopropylidenediphenol and α-chloroacetonitrile (0.80 mole) are added to a reactor. The reactor is heated and a clear solution forms at 56° C. The temperature is allowed to stabilize at 80° C., then a solution of sodium hydroxide (0.20 mole) and water (40.0 g) is added over a 68-minute period. The reaction continues at 80° C. for a total of 6.75 hours. Samples are taken after 4 and 6.75 hours of reaction and analyzed by gas chromatography to provide the following results:

| Sample Time (hr) | 4,4'-isopropyl-idenediphenol (%) | mono(cyano-methylated) (%) | di(cyano-methylated) (%) |
| --- | --- | --- | --- |
| 4.0 | 7.5 | 37 | 55.5 |
| 6.75 | 1.0 | 39 | 60.0 |

Substantial unreacted α-chloroacetonitrile is also observed.

(E) A reaction is completed using the method of Example 33(D), except that a solution of sodium hydroxide (0.20 mole) and water (15.0 g) is added over a 37-minute period. The reaction time is increased to a total of 84 hours. A sample is taken after 84 hours of reaction and analyzed by gas chromatography to provide the following results:

| Sample Time (hr) | 4,4'-isopropyl-idenediphenol (%) | mono(cyano-methylated) (%) | di(cyano-methylated) (%) |
| --- | --- | --- | --- |
| 84 | 4 | 37 | 59 |

Substantial unreacted α-chloroacetonitrile is also observed.

(F) A reaction is completed using the method of Example 33(D), except that a solution of sodium hydroxide (0.40 mole) and water (60.0 g) is added over a 52-minute period. After 23 hours of reaction at 80° C., the reaction temperature is increased to 100° C. The total reaction time is 46.5 hours. A pair of samples are taken after 6.33 and 46.5 hours of reaction and analyzed by gas chromatography to provide the following results:

| Sample Time (hr) | 4,4'-isopropyl-idenediphenol (%) | mono(cyano-methylated) (%) | di(cyano-methylated) (%) |
| --- | --- | --- | --- |
| 6.33 | 1 | 16 | 83 |
| 46.5 | 1 | 17 | 82 |

Substantial unreacted α-chloroacetonitrile is also observed.

(G) A reaction is completed using the method of Example 33(D), except that the reaction temperature is allowed to stabilize at 92° C. then a solution of sodium hydroxide (0.40 mole) and potassium iodide catalyst (0.04 mole) in water (70.0 g) is added over a 40-minute period. The reaction continues at a final temperature of 98° C. for 16 hours. Analysis of the product by gas chromatography provides the following results:

| Sample Time (hr) | 4,4'-isopropyl-idenediphenol (%) | mono(cyano-methylated) (%) | di(cyano-methylated) (%) |
| --- | --- | --- | --- |
| 16 | 1 | 17 | 82 |

Substantial unreacted α-chloroacetonitrile is also observed.

The chemistry of each of these comparative examples provides mixtures containing mono- and di(cyano-methylated) and unreacted 4,4'-isopropylidenediphenol. All of these reactions stagnate with respect to conversion resulting in comparatively low yields of the di(cyano-methylated) product.

EXAMPLE 34

(Not an embodiment of this invention)

One-tenth of a mole of 3,3',5,5'-tetrabromo-4,4'-isopropylidenediphenol and 0.40 mole of sodium hydroxide dissolved in 120.0 g of water are reacted under a nitrogen atmosphere to produce the disodium salt. The temperature of the clear solution is allowed to stabilize at 80° C. then 0.04 mole of tetramethylammonium chloride catalyst is added inducing slurry formation. α-Chloroacetonitrile (0.30 mole) is added over a 13-minute period. The initial α-chloroacetonitrile addition induces formation of a clear pale yellow refluxing solution. The reaction continues at 92° C.–95° C. for a total of 95 minutes. The organic layer is resolved and solidifies to a light amber solid at room temperature. This solid is dried under vacuum to a constant weight and analyzed by gas chromatography demonstrating the presence of 6 percent unreacted 3,3',5,5'-(tetrabromo-4,4'-isopropylidenediphenol, 25 percent mono(cyano-methylated) product and 69 percent di(cyano-methylated) product.

When compared to Examples 11 and 22, the mode of reaction described in this example whereby the phenate is preformed provides incomplete conversion of hydroxyaromatic reactant and less di(cyano-methylated) product.

EXAMPLE 35

(Not an embodiment of this invention)

A comparative example illustrative of the prior art cyanoethylation is completed as follows The novolak oligomer described in Example 16 (204 g), acrylonitrile (636 g) and 50 percent aqueous benzyltrimethylammonium hydroxide (24 g) are refluxed at 76° C. for 24 hours. The isolated product contains only 50 percent cyanoethylation based on phenolic titration. Considering these results, the prior art Michael addition of acrylonitrile to hydroxyaromatic reactants is not effective in producing a poly(cyano-ethylated) product.

What is claimed is:

1. A process for amido-alkylating or cyano-alkylating hydroxyaromatic compounds, which comprises:
   (a) in the presence of a catalyst and water, contacting a hydroxyaromatic compound with a haloamidohydrocarbylene or halocyanohydrocarbylene of the formula

wherein X is a halogen and $R_1$ and $R_2$ are independently hydrogen or $C_1$-$C_{10}$ alkyl; Y is —C≡N or

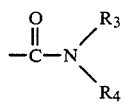

wherein $R_3$ and $R_4$ are independently H or $C_{1-10}$ alkyl; and
   (b) adding an alkaline agent to the mixture under conditions sufficient to form the corresponding amido- or cyano-alkylated aromatic compound.

2. The process of claim 1 wherein the hydroxyaromatic reactant is represented by the formula Ar—(OH)$_n$ wherein n is at least one and Ar is a mono- or polyvalent organic radical.

3. The process of claim 2 wherein the catalyst is selected from the group consisting of quaternary ammonium salts and, when Y is —C≡N, phosphonium salts.

4. The process of claim 3 wherein Ar is selected from the group consisting of:
   (a) aryl moieties having from 1 to 3 aromatic rings including fused ring systems; and
   (b) moieties of the formula

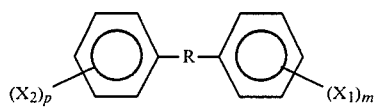

wherein R is optional and is selected from the group consisting of S, sulfoxide, sulfone, methylene, alkylidene, O, and aryl; wherein m and p have values selected independently from the range zero to 2; and wherein $X_1$ and $X_2$ are independently selected from the group consisting of halo, alkyl, nitro, and nitrile.

5. The process of claim 3 wherein the hydroxyaromatic compound is represented by the formula:

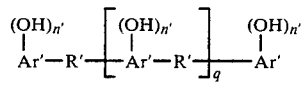

wherein R' is $C_1$-$C_3$ alkylene; n' is individually 0, 1 or 2; Ar' is a mono- or polyvalent organic radical selected from moieties having from 1 to 2 aromatic rings; and q is at least one.

6. The process of claim 4 or 5 wherein the alkaline agnet is NaOH or KOH.

7. The process of claim 6 wherein X is Cl or Br; either $R_1$ or $R_2$ is methyl, the other being H; and $R_3$ and $R_4$ are H when Y is not —C≡N.

8. The process of claim 7 wherein the catalyst is benzyltrimethylammonium chloride or tetramethylammonium chloride, the haloamidohydrocarbylene or halocyanohydrocarbylene is respectively 2-chloroacetamide or α-chloroacetonitrile, and the alkaline agent is NaOH.

9. The process of claim 3 wherein the catalyst is a polymer-supported quaternary ammonium or phosphonium salt.

10. The process of claim 9 wherein the catalyst is a polymer-supported quaternary ammonium salt.

11. The process of claim 8 wherein Ar' is a polyvalent organic radical having one aromatic ring, R' is methylene, n' is 1, the catalyst is benzyltrimethylammonium chloride, and the halocyanohydrocarbylene is α-chloroacetonitrile.

* * * * *

UNITED STATES PATENT AND TRADEMARK OFFICE
CERTIFICATE OF CORRECTION

PATENT NO. : 4,517,131

DATED : May 14, 1985

INVENTOR(S) : Robert E. Hefner, Jr.

It is certified that error appears in the above-identified patent and that said Letters Patent is hereby corrected as shown below:

Column 2, line 37, "indpendently" should read
-- independently --.

Column 5, line 29, "the" should read -- then --.

Column 8, line 68, "polycyano-methylated" should read
-- poly(cyano-methylated) --.

Column 10, lines 24, 26 and 31, "di(amide-methylated) should read -- di(amido-methylated) --.

Column 10, line 38, "the" should read -- then --.

Column 10, line 41, "at 110°C." should read
-- at the 110°C. --.

Column 10, line 61, "as follows" should read
-- as follows: --.

Column 14, line 37, "as follows" should read
-- as follows: --.

Column 16, line 43, "sion resulting" should read
-- sion, resulting --.

Column 16, line 63, "3,3',5,5'-(tetrabromo-" should read
-- 3,3',5,5'-tetrabromo- --.

Column 17, line 9, "as follows" should read
-- as follows: --.

UNITED STATES PATENT AND TRADEMARK OFFICE
CERTIFICATE OF CORRECTION

PATENT NO. : 4,517,131

DATED : May 14, 1985

INVENTOR(S) : Robert E. Hefner, Jr.

It is certified that error appears in the above-identified patent and that said Letters Patent is hereby corrected as shown below:

Column 18, Claim 6, line 32, "agnet" should read
-- agent --.

Column 9, line 6, "the The Dow" should read
-- The Dow --.

Title page, title of the patent should read
-- HIGH YIELD PROCESS FOR THE CYANOALKYLATION OR
AMIDOALKYLATION OF HYDROXYAROMATIC COMPOUNDS --.

Signed and Sealed this

Twenty-ninth Day of October 1985

[SEAL]

Attest:

DONALD J. QUIGG

Attesting Officer

Commissioner of Patents and
Trademarks—Designate